US005693594A

United States Patent [19]

Niedermann et al.

[11] Patent Number: 5,693,594
[45] Date of Patent: Dec. 2, 1997

[54] HERBICIDAL THIAZOLE DERIVATIVES

[75] Inventors: Hans-Peter Niedermann, Bubenheim, Germany; Dieter Gutheil, Bretzenheim, Germany

[73] Assignee: American Cyanamid Company, Madison, N.J.

[21] Appl. No.: 556,948

[22] PCT Filed: May 26, 1994

[86] PCT No.: PCT/EP94/01758

§ 371 Date: Apr. 25, 1996

§ 102(e) Date: Apr. 25, 1996

[87] PCT Pub. No.: WO94/27983

PCT Pub. Date: Dec. 8, 1994

[30] Foreign Application Priority Data

May 27, 1993 [EP] European Pat. Off. ............. 93108535

[51] Int. Cl.$^6$ ...................... C07D 277/56; A01N 43/78
[52] U.S. Cl. ...................... 504/266; 544/133; 546/280; 548/188
[58] Field of Search ............................ 548/188; 504/266

[56] References Cited

U.S. PATENT DOCUMENTS

| | | | |
|---|---|---|---|
| 4,298,375 | 11/1981 | Howe et al. | 71/90 |
| 4,501,894 | 2/1985 | Nezot | 548/180 |
| 5,055,477 | 10/1991 | Oda et al. | 514/341 |
| 5,128,481 | 7/1992 | Oda et al. | 548/377 |
| 5,244,867 | 9/1993 | Ditrich et al. | 504/266 |
| 5,256,633 | 10/1993 | Ditrich et al. | 504/266 |
| 5,284,821 | 2/1994 | Ditrich | 504/270 |

FOREIGN PATENT DOCUMENTS

| | | | |
|---|---|---|---|
| 0283762 | 2/1988 | European Pat. Off. | C07D 277/34 |
| 0419944A2 | 9/1990 | European Pat. Off. | C07D 263/34 |
| 0433899A1 | 12/1990 | European Pat. Off. | C07D 231/18 |

*Primary Examiner*—Robert Gerstl
*Attorney, Agent, or Firm*—Charles F. Costello, Jr.

[57] ABSTRACT

A compound of general formula (I) wherein: A represents a group of general formula (1) or (2) in which each X independently represents a halogen atom or an optionally substituted alkyl, cycloalkyl, alkoxy, aryl or aryloxy group, or an alkenyloxy, alkynyloxy, alkylthio, haloalkylthio, alkenylthio, alkynylthio, alkylsulphinyl, alkylsulphonyl or cyano group; and n is 0, an integer from 1 to 4, or, for the phenyl group, 5; or A represents a group of general formula (3) in which each of $R^4$, $R^5$ and $R^6$ independently represents a hydrogen or halogen atom, an optionally substituted alkyl, alkenyl, alkynyl, cycloalkyl, cycloalkylalkyl, aryl, aralkyl, alkaryl alkoxy, amino, mono- or di-alkylamino, alkoxycarbonylamino, arylamino, dialkylcarbamoyl, acyl or acylamido group or a cyano group, with the proviso that $R^5$ and $R^6$ do not represent an acyl, acylamido or cyano group; Z represents an oxygen or sulphur atom; $R^1$ and $R^2$ each independently represents a hydrogen atom or an optionally substituted alkyl, alkenyl, alkynyl, cycloalkyl, cycloalkylalkyl, heterocyclyl, aryl, aralkyl, alkaryl, hydroxy, alkoxy, alkenyloxy, alkynyloxy, alkylcarbonyl, alkoxycarbonyl, amino, mono- or di-alkylamino, alkoxycarbonylamino, arylamino, arylalkylamino or dialkylcarbamoyl group, or together represent an alkylene chain which is optionally interrupted by an oxygen or sulphur atom or by a group —NR— in which R represents a hydrogen atom or an alkyl group; and $R^3$ represents a hydrogen or halogen atom or an alkyl group.

6 Claims, No Drawings

HERBICIDAL THIAZOLE DERIVATIVES

This application is a 371 of PCT/EP94/01758 filed May 26, 1994.

The present invention relates to thiazole derivatives, their preparation and their use as herbicides.

The present invention provides a compound of the general formula

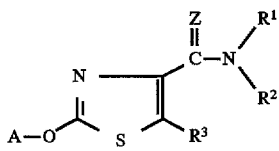

wherein

A represents a group of the general formula

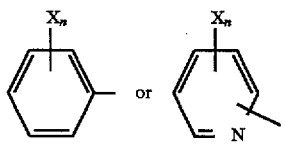

in which each X independently represents a halogen atom or an optionally substituted alkyl, cycloalkyl, alkoxy, aryl or aryloxy group, or an alkenyloxy, alkynyloxy, alkylthio, haloalkylthio, alkenylthio, alkynylthio, alkylsulphinyl, alkylsulphonyl or cyano group; and n is 0, an integer from 1 to 4, or, for the phenyl group, 5;

or A represents a group of the general formula

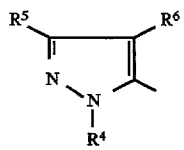

in which each of $R^4$, $R^5$ and $R^6$ independently represents a hydrogen or halogen atom, an optionally substituted alkyl, alkenyl, alkynyl, cycloalkyl, cycloalkylalkyl, aryl, aralkyl, alkaryl, alkoxy, amino, mono- or di-alkylamino, alkoxycarbonylamino, arylamino, dialkylcarbamoyl, acyl or acylamido group or a cyano group, with the proviso that $R^5$ and $R^6$ do not represent an acyl, acylamido or cyano group.

Z represents an oxygen or sulphur atom;

$R^1$ and $R^2$ each independently represents a hydrogen atom or an optionally substituted alkyl, alkenyl, alkynyl, cycloalkyl, cycloalkylalkyl, heterocyclyl, aryl aralkyl, alkaryl, hydroxy, alkoxy, alkenyloxy, alkynyloxy, alkylcarbonyl, alkoxycarbonyl, amino, mono- or di-alkylamino, alkoxycarbonylamino, arylamino, arylalkylamino or dialkylcarbamoyl group, or together represent an alkylene chain which is optionally interrupted by an oxygen or sulphur atom or by a group —NR— in which R represents a hydrogen atom or an alkyl group; and $R^3$ represents a hydrogen or halogen atom or an alkyl group.

EP-A-0419944 discloses somewhat similar herbicidal thiazole derivatives but with different substitution at the 5-position of the thiazole ring.

EP-A-283762 also discloses herbicidal thiazole derivatives but lacking a carboxamide or thiocarboxamide group at the 4-position of the thiazole ring.

Generally, herein, any alkyl, alkenyl or alkynyl moiety which is or forms part of a group represented by X, $R^1$, $R^2$, $R^3$, $R^4$, $R^5$ or $R^6$, suitably contains up to 12 carbon atoms, conveniently up to 8, preferably up to 6, and especially up to 4, carbon atoms. Such moieties may be linear or branched chain moieties. As part of a larger group, alkyl moieties are especially methyl or ethyl.

A cycloalkyl moiety suitably contains from 3 to 10, preferably from 3 to 8, carbon atoms. An aryl group is usefully a single ring or fused ring system having from 6 to 14 ring members, preferably 6 or 10 ring atoms; a preferred aryl group is phenyl. A heterocyclic group is suitably a single ring system having 5 or 6 ring members selected from carbon atoms and at least one nitrogen, oxygen or sulphur atom; preferred heterocyclic groups are morpholino and thienyl.

Halogen is used to denote fluorine, chlorine, bromine or iodine, especially chlorine or fluorine. A preferred haloalkyl moiety is trifluoromethyl.

An acyl group is the group formed by the removal of hydroxyl from a carboxyl group, and is used herein to include formyl and optionally substituted alkylcarbonyl and arylcarbonyl groups.

An alkylene chain suitably has from 3 to 6, preferably 4 or 5 chain members.

Optional substituents may be any of those customarily employed in the development of biocidal compounds, and/or the modification of such compounds to influence their activity, persistence, penetration or any other property. Specific examples of such substituents include halogen, especially fluorine, chlorine or bromine atoms, and phenyl, nitro, cyano, amino, hydroxy, alkyl, alkoxy, mono- or di-alkylamino groups, haloalkyl, haloalkoxy, cycloalkyl, formyl, alkoxycarbonyl, carboxy, halophenyl groups and heterocyclyl, especially thienyl, groups. Alkyl moieties of such optional substituents usefully have from 1 to 6 carbon atoms, preferably 1 or 2 carbon atoms.

Where A represents an optionally substituted phenyl or pyridyl ring, the substituent(s) X, if present, may be at any of the free positions on the ring. Preferably a substituent X is present meta to the bond to the oxygen atom of formula I. Especially useful examples of the substituent(s) X include halogen atoms and haloalkyl groups. Preferably X represents a chlorine atom or a trifluoromethyl group. There are usefully either no X substituents or, preferably, only 1 such substituent.

Where A represents a pyrazolyl group, preferably $R^6$ represents a hydrogen atom, and each of $R^4$ and $R^5$ independently represents an alkyl, haloalkyl or an aryl group, more preferably a $C_{1-4}$ alkyl, or halo($C_{1-2}$) alkyl group, especially a methyl or trifluoroalkyl group. Preferably, $R^4$ represents a methyl group and $R^5$ represents a methyl or trifluoromethyl group; it is especially preferred that $R^4$ represents a methyl group and $R^5$ represents a trifluoromethyl group.

Z preferably represents an oxygen atom.

Preferably, $R^3$ represents a hydrogen atom or a methyl group.

The substituents $R^1$ and $R^2$ may be the same or different. Preferably each of $R^1$ and $R^2$ independently represents a hydrogen atom, or a $C_{1-8}$ alkyl group which is unsubstituted or substituted by one or more of the same or different substituents selected from halogen atoms, phenyl and thienyl groups, a $C_{1-6}$ alkoxy group, a $C_{3-8}$ cycloalkyl group, a $C_{3-12}$ cycloalkylalkyl group, a morpholino group, or a phenyl group which is unsubstituted or substituted by one or more of the same or different halogen atoms.

More preferably, one of $R^1$ and $R^2$ represents a hydrogen atom or a $C_{1-4}$ alkyl group, for example ethyl, and the other represents a $C_{1-6}$ alkyl group, for example methyl, isopropyl, n-propyl, n- or s-butyl, or pentyl, a $C_{1-4}$ fluoroalkyl group, especially mono- or tri-fluoroethyl, a phen($C_{1-2}$)alkyl group, especially benzyl or phenylethylidene, a thienyl($_{1-2}$)alkyl group, especially thien-2-ylethylidene, a cyclopropyl($C_{1-2}$) alkyl group, especially cyclopropylmethyl, a $C_{1-4}$ alkoxy group, for example t-butoxy, a cyclopropyl, cyclobutyl, morpholino, or phenyl group, or a mono- or di-fluorophenyl group, for example 2-, 3- or 4-fluorophenyl or 2,4-difluorophenyl. Especially preferred are compounds in which one of $R^1$ and $R^2$ is hydrogen or ethyl and the other is phenyl, 4-fluorophenyl or 2,4-difluorophenyl.

The present invention further provides a process for the preparation of a compound of general formula I, which comprises reacting a compound of the general formula II

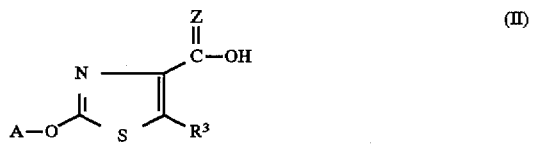

in which $R^3$, A and Z are as defined in above, or an activated derivative thereof, with a compound of the general formula III

HNR$^1$R$^2$      (III)

in which $R^1$ and $R^2$ are as defined above.

Activated derivatives of the compounds of the general formula II are compounds in which the hydroxy group of the acid function has been replaced by a suitable leaving group. A leaving group is any group that will, under the reaction conditions, cleave from the starting material, thus enabling substitution at that specific site. The leaving group may suitably be a halogen atom, for example a bromine atom or, especially a chlorine atom, an alkoxy group, suitably $C_{1-4}$ alkoxy, especially methoxy, an imidazole group, an alkyl- or aryl-sulphonium group, especially a $C_{1-6}$ alkyl-, phenyl- or tolyl-sulphonium group, or an alkyl- or aryl-sulphonic acid group, especially a $C_{1-6}$ alkyl-, phenyl- or tolyl-sulphonic acid group. Preparation of an activated derivative may be effected by conventional means, for example the acid chloride may be prepared using thionyl chloride.

The process of the invention is suitably carried out in the presence of an inert organic solvent, for example dimethylformamide or dimethylsulphoxide, or an aromatic hydrocarbon, for example benzene or toluene, or a halogenated hydrocarbon, for example dichloromethane, or an ether, for example diethyl ether, or an ester, for example ethyl acetate. The process is suitably carried out at a temperature in the range of from 0° to 100° C., preferably at the reflux temperature of the reaction mixture, and suitably in the presence of a base, for example potassium hydroxide, and a copper catalyst, such as cuprous chloride.

Suitably the reaction is carried out using substantially equimolar amounts of the reactants. However, it can be expedient to use one reactant in excess.

When the compounds of formula I are prepared from an acid halide derivative of the compound of formula II, the reaction is conveniently carried out at a temperature in the range of from 0° to 50° C., preferably at ambient temperature, and suitably in the presence of a base, for example potassium carbonate or, preferably, an amine base, such as triethylamine.

Other activated derivatives may require different reaction conditions which will be within the knowledge of the skilled person in the art, or easily ascertainable by such by routine experimentation. For an ester derivative (where the hydroxy function has been replaced by an alkoxy group), the reaction is suitably carried out at a temperature in the range of from 0° to 100° C., preferably at ambient temperature, and in the absence of an added base.

Compounds of formula I in which Z represents a sulphur atom may be prepared from a compound of formula I in which Z represents an oxygen atom by reaction with phosphorous pentasulphide under standard conditions, for example by heating, suitably under reflux, in the presence of an inert aromatic solvent, for example benzene, toluene, pyridine or quinoline.

The compounds of the present invention may be isolated and purified by conventional techniques, for example by solvent extraction, evaporation followed by recrystallisation, or by chromatography on silica or alumina.

The compounds of formula II are preferably prepared by reacting a compound of the general formula IV

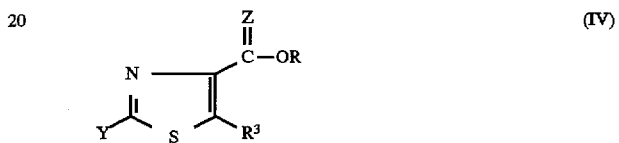

in which Z and $R^3$ are as specified above, Y represents a leaving group, preferably a halogen atom, for example bromine, and R represents an alkyl group, for example an ethyl group, with a compound of the formula V

A—OM      (V)

in which A is an optionally substituted phenyl, pyridyl or pyrazolyl group as hereinbefore defined, and M represents a hydrogen atom or an alkali metal atom, especially a sodium atom.

The compounds of the general formula IV may be prepared by the deamination and activation of compounds of the general formula VI

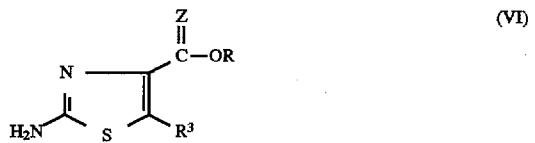

in which $R^3$, Z and R are as defined above using sodium nitrite and an appropriate activating agent to provide the leaving group Y; thus for Y as bromine an appropriate agent is hydrogen bromide. Such procedures should be carried out with care at a temperature below 0° C., for example at from −10° to −20° C., using an appropriate liquid reaction medium, for example water.

Compounds of the formula VI may be prepared by the thiazole preparation procedure of reacting an alkyl pyruvate with thiourea in a solution of ethanol, at reflux.

The compounds of formula V are either known or preparable by conventional or literature methods. For example, the compounds of formula V are preparable by the methods of, for example, J. Het. Chem. 28 (1991), 1971 ff, and J. Het. Chem. 27 (1990), 243 ff.

The compounds of formula II, and their ester derivatives, are novel compounds and form another aspect of this invention.

Compounds of formula I have been found to have useful herbicidal activity. Accordingly, the present invention further provides a herbicidal composition which comprises a compound of formula I in association with a carrier, and a method of making such a composition which comprises bringing a compound of formula I into association with a carrier.

The invention further provides the use of a compound of formula I or of a composition of the invention, as a herbicide. Also provided is a method of combating undesired plant growth at a locus by treating the locus with a compound of formula I or a composition of the invention. The locus may be, for example, the soil or plants in a crop area. The dosage of active ingredient used may, for example, be in the range of from 0.01 to 10 kg/ha.

A carrier in a composition according to the invention is any material with which the active ingredient is formulated to facilitate application to the locus to be treated, which may for example be a plant, seed or soil, or to facilitate storage, transport or handling. A carrier may be a solid or a liquid, including a material which is normally gaseous but which has been compressed to form a liquid, and any of the carriers normally used in formulating herbicidal compositions may be used. Preferably compositions according to the invention contain 0.5 to 95% by weight of active ingredient.

Suitable solid carriers include natural and synthetic clays and silicates, for example natural silicas such as diatomaceous earths; magnesium silicates, for example talcs.; magnesium aluminium silicates, for example attapulgites and vermiculites; aluminium silicates, for example kaolinites, montmorillonites and micas; calcium carbonate; calcium sulphate; ammonium sulphate; synthetic hydrated silicon oxides and synthetic calcium or aluminium silicates; elements, for example carbon and sulphur; natural and synthetic resins, for example coumarone resins, polyvinyl chloride, and styrene pollers and copolymers; solid polychlorophenols; bitumen; waxes; and solid fertilisers, for example superphosphates.

Suitable liquid carriers include water; alcohols, for example isopropanol and glycols; ketones, for-example acetone, methyl ethyl ketone, methyl isobutyl ketone and cyclohexanone; ethers; aromatic or araliphatic hydrocarbons, for example benzene, toluene and xylene; petroleum fractions, for example kerosine and light mineral oils; chlorinated hydrocarbons, for example carbon tetrachloride, perchloroethylene and trichloro-ethane. Mixtures of different liquids are often suitable.

Agricultural compositions are often formulated and transported in a concentrated form which is subsequently diluted by the user before application. The presence of small amounts of a carrier which is a surface-active agent facilitates this process of dilution. Thus preferably at least one carrier in a composition according to the invention is a surface-active agent. For example the composition may contain at least two carriers, at least one of which is a surface-active agent.

A surface-active agent may be an emulsifying agent, a dispersing agent or a wetting agent; it may be nonionic or ionic. Examples of suitable surface-active agents include the sodium or calcium salts of polyacrylic acids and lignin sulphonic acids; the condensation products of fatty acids or aliphatic amines or amides containing at least 12 carbon atoms in the molecule with ethylene oxide and/or propylene oxide; fatty acid esters of glycerol, sorbitol, sucrose or pentaerythritol; condensates of these with ethylene oxide and/or propylene oxide; condensation products of fatty alcohol or alkyl phenols, for example p-octylphenol or p-octylcresol, with ethylene oxide and/or propylene oxide; sulphates or sulphonates of these condensation products; alkali or alkaline earth metal sales, preferably sodium salts, of sulphuric or sulphonic acid esters containing at least 10 carbon atoms in the molecule, for example sodium lauryl sulphate, sodium secondary alkyl sulphates, sodium salts of sulphonated castor oil, and sodium alkylaryl sulphonates such as dodecylbenzene sulphonate; and polymers of ethylene oxide and copolymers of ethylene oxide and propylene oxide.

The compositions of the invention may for example be formulated as wettable powders, dusts, granules, solutions, emulsifiable concentrates, emulsions, suspension concentrates and aerosols. Wettable powders usually contain 25, 50 or 75% w of active ingredient and usually contain in addition to solid inert carrier, 3–10% w of a dispersing agent and, where necessary, 0–10% w of stabiliser(s) and/or other additives such as penetrants or stickers. Dusts are usually formulated as a dust concentrate having a similar composition to that of a wettable powder but without a dispersant, and are diluted in the field with further solid carrier to give a composition usually containing ½–10% w of active ingredient. Granules are usually prepared to have a size between 10 and 100 BS mesh (1.676–0.152 mm), and may be manufactured by agglomeration or impregnation techniques. Generally, granules will contain ½–75% w active ingredient and 0–10% w of additives such as stabilisers, surfactants, slow release modifiers and binding agents. The so-called "dry flowable powders" consist of relatively small granules having a relatively high concentration of active ingredient. Emulsifiable concentrates usually contain, in addition to a solvent and, when necessary, co-solvent, 10–50% w/v active ingredient, 2–20% w/v emulsifiers and 0–20% w/v of other additives such as stabilisers, penetrants and corrosion inhibitors. Suspension concentrates are usually compounded so as to obtain a stable, non-sedimenting flowable product and usually contain 10–75% w active ingredient, 0.5–15% w of dispersing agents, 0.1–10% w of suspending agents such as protective colloids and thixotropic agents, 0–10% w of other additives such as defoamers, corrosion inhibitors, stabilisers, penetrants and stickers, and water or an organic liquid in which the active ingredient is substantially insoluble; certain organic solids or inorganic salts may be present dissolved in the formulation to assist in preventing sedimentation or as anti-freeze agents for water.

Aqueous dispersions and emulsions, for example compositions obtained by diluting a wettable powder or a concentrate according to the invention with water, also lie within the scope of the invention. The said emulsions may be of the water-in-oil or of the oil-in-water type, and may have a thick 'mayonnaise'-like consistency.

The composition of the invention may also contain other ingredients, for example compounds possessing insecticidal or fungicidal properties or other herbicides.

The following examples illustrate the invention. All structures were confirmed by mass spectroscopy and/or 300'H nmr. Examples 1 and 3 to 7 are concerned with the preparation of compounds of general formula II, Examples 2 and 8 to 56 concern the preparation of compounds of the general formula I.

EXAMPLES 1 TO 56

EXAMPLE 1

Preparation of ethyl-2-(3-chlorophenoxy)thiazole-4-carboxylate

Example 1a)—Preparation of ethyl-2-aminothiazole-4-carboxylate 42.15 g (554 mmol) thiourea was dissolved in 1000 ml hot ethanol and the solution cooled in an ice bath to 6° to 8° C., whereupon the thiourea partly crystallized. Over a period of 1 hour 100 g (451.5 mmol) of ethyl 2-bromopyruvate was added to this solution whilst maintaining the temperature below 10° C. After the addition has been completed the solution was refluxed for 2 hours, cooled to room temperature and made alkaline by the addition of 250 ml of 25% ammonia in water. The solution was cooled to 5° C. The solid was collected, washed with 50 ml cold ethanol and dried to give 65.6 g (82.1%) of pale yellow ethyl-2-aminothiazole-4-carboxylate (m.p. 167°–168° C.).

Example 1b)—Preparation of ethyl-2-bromothiazole-4-carboxylate

A solution of 30 g (174.3 mmol) ethyl-2-aminothiazole-4-carboxylate [prepared as in Example 1a)] in a mixture of 100 ml HBr (65%) and 100 ml of water was cooled to −15° C. and a solution of 12.03 g (174.3 mmol) sodium nitrite in 40 ml water was added over a period of 30 minutes and the mixture stirred for another 30 minutes at −15° C. After warming to room temperature, the solid was collected, washed with 50 ml cold water and dried to give 23.7 g (57.6%) ethyl-2-bromothiazole-4-carboxylate m.p. 63°–65° C.

Example 1c) Preparation of ethyl-2-(3-chlorophenoxy)thiazole-4-carboxylate 13.72 g (106.72 mmol) 3-chlorophenol were added to a mixture of 19.21 g (106.72 mmol) sodium methylate-solution (30% in methanol) and 200 ml toluene and the mixture stirred 15 minutes at room temperature. The solution was evaporated to dryness, the residue suspended in 100 ml of toluene and evaporated to dryness again. The residue was dissolved in 100 ml dimethylsulphoxide and 24 g (101.65 mmol) of ethyl-2-bromothiazole-4-carboxylate [prepared as in Example 1b] were added in one portion. The solution was stirred for 24 hours at 80° C., cooled to room temperature and poured into 1200 ml water. 200 ml of saturated sodium chloride solution were added and the mixture extracted three times with 300 ml toluene. The organic layers were combined and washed with 200 ml 0.1 m NaOH and 200 ml of diluted sodium chloride solution, dried over $Na_2SO_4$ and evaporated to dryness to give 27.72 g (96%) of pale brown oily ethyl-2-(3-chlorophenoxy)thiazole-4-carboxylate. NMR $(CDCl_3)$:1.35(t,3H,$CH_3$); 4.4 (q,2H,$CH_2$); 7.3(m,4H,Arom.) 7.7(s,1H,arom.).

EXAMPLE 2

Preparation of 2-(3-chlorophenoxy)thiazole-4-carboxanilide

Example 2a)—Preparation of 2-(3-chlorophenoxy)thiazole-4-carboxylic acid

A mixture of 26,36g (92.9 mmol) ethyl-2-(3-chlorophenoxy)thiazole-4-carboxylate (prepared analogously to the procedures of Example 1c), 7.5 g (187.5 mmol) NaOH and 300 ml of water was stirred 1 hour at 60° C. and 16 hours at room temperature. After adding a small amount of charcoal the yellow solution was stirred 10 minutes at room temperature and the charcoal separated by silica gel filtration. The filtrate was acidified with conc. HCl and the precipitate was collected and dried to give 22.5 g (94.7%) of 2-(3-chlorophenoxy)thiazole-4-carboxylic acid of m.p. 135°–137° C.

Example 2b)—Preparation of 2-(3-chlorophenoxy)thiazole-4-carboxanilide 1 g (3.75 mmol) 2-(3-chlorophenoxy)thiazole-4-carboxylic acid was added to 1 ml of $SOCl_2$ and refluxed until the mixture gave a clear solution. Excess $SOCl_2$ was evaporated in vacuo and the remaining acid chloride dissolved in 25 ml toluene. To this solution was added a solution of 0.34 g (3.65 mmol) aniline and 0.37 g triethylamine in 20 ml toluene. After stirring over night at room temperature the solution was washed with 20 ml dil. HCl, 20 ml water, 20 ml dil. NaOH and 20 ml water. The organic layer was dried with $NaSO_4$ and evaporated to dryness to give 1.0 g (82.8%) 2-(3-chlorophenoxy)thiazole-4-carbanilide (m.p.:94°–95° C.).

The same procedures have been followed for the preparation of the examples in Table 1 for the 5-methyl compounds, starting with ethyl 2-amino-5-methylthiazole-4-carboxylate and for the 5-bromo compounds, starting from ethyl 2,5-dibromothiazole-4-carboxylate.

EXAMPLES 3 TO 56

By procedures analogous to the above, further compounds were prepared, details of which are given below. Examples 3 to 7 were carried out analogously to Example 1c above; Examples 8 and 9 were carried out analogously to Example 2a) above; Examples 10 to 56 were carried out analogously to Example 2b) above. The 5-methyl compounds of Examples 25 to 29 and 35 to 39 were prepared using the initial starting material of ethyl-2-amino-5-methylthiazole-4-carboxylate.

TABLE 1

2-substituted ethyl thiazole-4-carboxylates $$\begin{array}{c}\text{RO}-\overset{\overset{\displaystyle O}{\|}}{C}\\ \diagdown\\ \phantom{xx}\diagup\phantom{x}\diagdown\\ R^3\phantom{xxxx}S\phantom{xx}\diagdown\\ \phantom{xxxxxxxxxx}O-A\end{array}$$

| Ex. No. | $R^3$ | A | R | m.p. (°C.) | yield (%) |
|---|---|---|---|---|---|
| 3 | H | 3-$CF_3$-phenyl | $C_2H_5$ | oil | 50.7 |
| 4 | $CH_3$ | 3-$CF_3$-phenyl | $CH_3$ | oil | 50.5 |
| 5 | H | 3-$CF_3$-1-methylpyrazol-5-yl | $C_2H_5$ | 90–92 | 73.0 |
| 6 | H | 3-Cl-pyridin-2-yl | $C_2H_5$ | 78–80 | 46.2 |
| 7(A) | H | 3,5-diCl-phenyl | $C_2H_5$ | 68–70 | 63.5 |

TABLE 1-continued 2-substituted ethyl thiazole-4-carboxylates

| Ex. No. | $R^3$ | A | R | m.p. (°C.) | yield (%) |
|---|---|---|---|---|---|
| 7(B) | H | 3-Cl-C$_6$H$_4$ | C$_2$H$_5$ | oil | 96.0 |
| 7(C) | Br | 3-CF$_3$-C$_6$H$_4$ | C$_2$H$_5$ | oil | 59.2 |

NMR data (CDCl$_3$) on compounds isolated as oils:-
Example 3: 1.35(t, 3H, CH$_3$); 4.35(q, 2H, CH$_2$); 7.5(m, 4H, Arom.); 7.75(s, 1H, Arom.).
Example 4: 2.7(s, 3H, CH$_3$); 4.85(s, 3H, CH$_3$); 7.5(m, 4H, Arom.).
Example 7(C) 1.35(t, 3H, CH$_3$); 4.35(q, 2H, CH$_2$); 7.55(m, 4H, Arom.).

TABLE 2

2-substituted thiazole-4-carboxylic acids

| Ex. No. | $R^3$ | A | m.p. (°C.) | yield (%) |
|---|---|---|---|---|
| 8 | H | 3-CF$_3$-C$_6$H$_4$ | 128–129 | 90.3 |
| 9(A) | H | 3-Cl-C$_6$H$_4$ | 135–137 | 94.7 |
| 9(B) | H | 2,4-Cl$_2$-C$_6$H$_3$ | 174 | 90.8 |
| 9(C) | H | 3-CF$_3$-pyrazolyl | 176–181 | 70.0 |

TABLE 2-continued 2-substituted thiazole-4-carboxylic acids

| Ex. No. | $R^3$ | A | m.p. (°C.) | yield (%) |
|---|---|---|---|---|
| 9(D) | Br | 3-CF$_3$-C$_6$H$_4$ | 110 | 91.9 |

TABLE 3

2-(3-trifluoromethylphenoxy)thiazole-4-carboxamides

| Ex. No. | $R_1$ | $R_2$ | m.p. (°C.) | yield (%) |
|---|---|---|---|---|
| 10 | H | cyclopropyl | 80 | 76.8 |
| 11 | H | CH(CH$_3$)$_2$ | 81 | 76.4 |
| 12 | H | 4-F-C$_6$H$_4$ | 96 | 72.4 |
| 13 | H | 2,4-F-C$_6$H$_3$ | 98 | 71.7 |
| 14 | C$_2$H$_5$ | C$_6$H$_5$ | oil | 78.4 |
| 15 | H | n-C$_4$H$_9$ | 68 | 85.0 |
| 16 | H | CH$_2$CH(CH$_3$)$_2$ | 93–94 | 81.6 |
| 17 | H | CH$_2$C(CH$_3$)$_3$ | 64–65 | 89.0 |
| 18 | H | CH$_3$ | 109–110 | 80.0 |
| 19 | H | CH$_2$CF$_3$ | 58 | 67.0 |
| 20 | H | CH(CH$_3$)(C$_6$H$_5$) | 79 | 65.1 |
| 21 | H | CH(CH$_3$)(2-thienyl) | 107 | 57.9 |
| 22 | H | CH$_2$CH$_2$F | 77–78 | 51.4 |
| 23 | H | OC(CH$_3$)$_3$ | 92–93 | 38.4 |
| 24 | H | N-morpholino | 98–99 | 79.1 |

Ex. 14 NMR (CDCl$_3$): 1.1(t, 3H, CH$_3$); 3.85(q, 2H, CH$_2$); 6.9–7.6(m, 10H, Arom.)

TABLE 4

2-(3-trifluoromethylphenoxy)-5-methylthiazole-4-carboxamides

| Ex. No. | $R_1$ | $R_2$ | m.p. (°C.) | yield (%) |
|---|---|---|---|---|
| 25 | H | 2,4-F-C$_6$H$_3$ | 98–101 | 83.6 |
| 26 | H | 4-F-C$_6$H$_4$ | 69 | 81.0 |
| 27 | C$_2$H$_5$ | C$_6$H$_5$ | oil | 85.0 |
| 28 | H | CH(CH$_3$)$_2$ | 68 | 83.0 |
| 29 | H | cyclopropyl | 69 | 78.0 |

Ex. 27. NMR(CDCl$_3$): 1.1(t, 3H, CH$_3$); 2.4(s, 3H, CH$_2$); 3.8(q, 2H, CH$_2$); 6.9(m, 2H, Arom.); 7.2(m, 5H, Arom.); 7.35(m, 2H, Arom.)

TABLE 5

2-(1-methyl-3-trifluoromethylpyrazol-5-yloxy)-thiazole-4-carboxamides

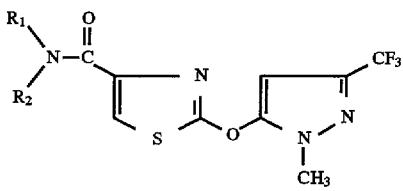

| Ex. No. | $R_1$ | $R_2$ | m.p. (°C.) | yield (%) |
|---|---|---|---|---|
| 30 | H | cyclopropyl | 114–115 | 70.6 |
| 31 | H | $CH(CH_3)_2$ | 103 | 70.2 |
| 32 | H | $4\text{-}F\text{-}C_6H_4$ | 120–121 | 68.0 |
| 33 | H | $2,4\text{-}F\text{-}C_6H_3$ | 125–126 | 69.0 |
| 34 | $C_2H_5$ | $C_6H_5$ | 78–80 | 69.6 |

TABLE 6

2-(1-methyl-3-trifluoromethylpyrazol-5-yloxy)-5-methylthiazole-4-carboxamides

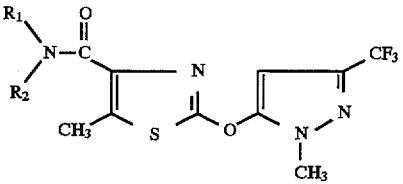

| Ex. No. | $R_1$ | $R_2$ | m.p. (°C.) | yield (%) |
|---|---|---|---|---|
| 35 | H | $4\text{-}F\text{-}C_6H_4$ | 139 | 81.0 |
| 36 | H | $2,4\text{-}F\text{-}C_6H_3$ | 145–47 | 87.0 |
| 37 | $C_2H_5$ | $C_6H_5$ | 65–66 | 93.0 |
| 38 | H | $CH(CH_3)_2$ | 83–85 | 84.7 |
| 39 | H | cyclopropyl | 94–96 | 80.0 |

TABLE 7

2-(2,4-Dichlorophenoxy)thiazole-4-carboxamides

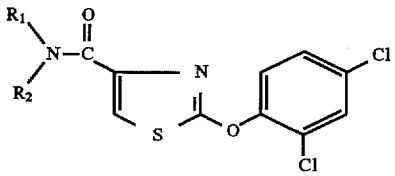

| Ex. No | $R_1$ | $R_2$ | m.p. (°C.) | yield (%) |
|---|---|---|---|---|
| 40 | $C_2H_5$ | $C_6H_5$ | oil | 88.5 |
| 41 | H | $CH(CH_3)_2$ | 65 | 75.0 |
| 42 | H | cyclopropyl | 116–117 | 75.0 |
| 43 | H | cyclobutyl | 105 | 77.3 |
| 44 | H | $n\text{-}C_4H_9$ | 83–85 | 78.0 |
| 45 | H | n-morpholino | 116–117 | 67.0 |
| 46 | H | $i\text{-}C_4H_9$ | 95–96 | 78.0 |
| 47 | H | $OC(CH_3)_3$ | oil | 55.8 |
| 48 | H | $CH_2$-cyclopropyl | 72–73 | 78.4 |
| 49(A) | H | $n\text{-}C_3H_7$ | 75 | 80.6 |
| 49(B) | H | $C_6H_5$ | 98–100 | 83.4 |
| 49(C) | H | $4\text{-}F_2\text{-}C_6H_4$ | 110–112 | 80.2 |
| 49(D) | H | $2,4\text{-}F\text{-}C_6H_3$ | 136–139 | 79.5 |
| 49(E) | H | $CH_2C_6H_5$ | 113–114 | 83.4 |
| 49(F) | H | $3\text{-}F\text{-}C_6H_4$ | 111 | 78.9 |
| 49(G) | H | $2\text{-}F\text{-}C_6H_4$ | 152–154 | 73.3 |

TABLE 7-continued 2-(2,4-Dichlorophenoxy)thiazole-4-carboxamides

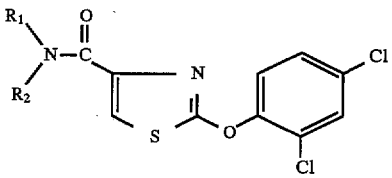

| Ex. No | $R_1$ | $R_2$ | m.p. (°C.) | yield (%) |
|---|---|---|---|---|

NMR data ($CDCl_3$) on compounds isolated as oils:
Example 40: 1.1(t, 3H, $CH_3$); 3.8(q, 2H, $CH_2$); 7.2(m, 9H, Arom.).
Example 47: 1.25(s, 9H, $CH_3$); 7.3(m, 2H, Arom.); 7.5(m, 1H, arom.); 7.7(s, 1H, Arom.); 8.85(s, 1H, NH).

TABLE 8

2-(3-chlorophenoxy)thiazole-4-carboxamides

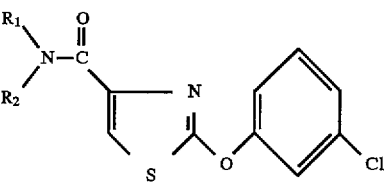

| Ex. No. | $R_1$ | $R_2$ | m.p. (°C.) | yield (%) |
|---|---|---|---|---|
| 50 | H | $C_6H_4$ | 94–95 | 82.8 |
| 51 | H | $2\text{-}F\text{-}C_6H_4$ | 115 | 80.0 |
| 52 | H | $3\text{-}F\text{-}C_6H_4$ | 74–75 | 80.0 |
| 53 | H | $4\text{-}F\text{-}C_6H_4$ | 115 | 80.0 |
| 54 | H | $2,4\text{-}di\text{-}F\text{-}C_6H_3$ | 110 | 86.9 |
| 55 | $C_2H_5$ | $C_6H_5$ | 65 | 80.6 |
| 56 | H | $CH_2C_6H_5$ | 98–99 | 73.3 |

TABLE 9

2-(3-trifloromethylphenoxy)-5-bromothiazole-4-carboxamides

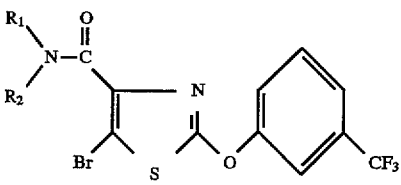

| Ex. No. | $R_1$ | $R_2$ | m.p. (°C.) | yield (%) |
|---|---|---|---|---|
| 57 | H | $4\text{-}F\text{-}C_6H_4$ | 104 | 80.0 |
| 58 | H | $2,4\text{-}di\text{-}F\text{-}C_6H_3$ | 85 | 78.9 |
| 59 | $C_2H_5$ | $C_6H_5$ | 54 | 91.0 |
| 60 | H | $cyclo\text{-}C_3H_5$ | 82–84 | 75.4 |

EXAMPLE 61

Herbicidal Activity

To evaluate their herbicidal activity, compounds according to the invention were tested using as representative range of plants: maize, *Zea mays* (Mz); rice, *Oryza sativa* (R); barnyard grass, *Echinochloa crusgalli* (BG); oat, *Avena sativa* (0); linseed, *Linum usitatissimum* (L); mustard, *Sinapsis alba* (M); sugar beet, *Beta vulgaris* (SB) and soya bean, *Glycine max* (S).

The tests fall into two categories, pre-emergence and post-emergence. The pre-emergence tests involved spraying a liquid formulation of the compound onto the soil in which the seeds of the plant species mentioned above had recently been sown. The post-emergence tests involved two types of test, viz., soil drench and foliar spray tests. In the soil drench tests the soil in which the seedling plants of the above species were growing was drenched with a liquid formulation containing a compound of the invention, and in the foliar spray tests the seedling plants were sprayed with such a formulation.

The soil used in the tests was a prepared horticultural loam.

The formulations used in the tests were prepared from solutions of the test compounds in acetone containing 0.4% by weight of an alkylphenol/ethylene oxide condensate available under the trade mark TRITON X-155. These acetone solutions were diluted with water and the resulting formulations applied at dosage levels corresponding to 5 kg or 1 kg of active material per hectare in a volume equivalent to 600 liters per hectare in the soil spray and foliar spray test, and at a dosage of level equivalent to 10 kilograms of active material per hectare in a volume equivalent to approximately 3,000 liters per hectare in the soil drench tests.

In the pre-emergence tests untreated sown soil and in the post-emergence tests untreated soil bearing seedling plants were used as controls.

The herbicidal effects of the test compounds were assessed visually twelve days after spraying the foliage and the soil, and thirteen days after drenching the soil and were recorded on a 0–9 scale. A rating 0 indicates growth as untreated control, a rating 9 indicates death. An increase of 1 unit on the linear scale approximates to a 10% increase in the level of effect.

The results of the tests are set out in Table 9 below, in which the compounds are identified by reference to the preceding Examples.

TABLE 9

| Compound of Ex. No. | Soil drench 10 kg/ha | | | | | | | | Dosage kg/ha | Foliar spray | | | | | | | | Pre-emergence | | | | | | | |
|---|---|---|---|---|---|---|---|---|---|---|---|---|---|---|---|---|---|---|---|---|---|---|---|---|---|
| | Mz | R | BG | O | L | M | SB | S | | Mz | R | BG | O | L | M | SB | S | Mz | R | BG | O | L | M | SB | S |
| 1c | 0 | 0 | 0 | 0 | 0 | 0 | 0 | 0 | 5 | 0 | 0 | 5 | 0 | 0 | 4 | 9 | 0 | 0 | 0 | 0 | 0 | 0 | 0 | 0 | 0 |
| | | | | | | | | | 1 | 0 | 0 | 0 | 0 | 0 | 0 | 5 | 0 | 0 | 0 | 0 | 0 | 0 | 0 | 0 | 0 |
| 10 | 0 | 0 | 0 | 0 | 0 | 0 | 0 | 0 | 5 | 5 | 2 | 8 | 4 | 8 | 9 | 9 | 7 | 0 | 0 | 7 | 0 | 2 | 4 | 7 | 0 |
| | | | | | | | | | 1 | 4 | 0 | 4 | 2 | 7 | 8 | 8 | 6 | 0 | 0 | 2 | 0 | 0 | 2 | 2 | 0 |
| 11 | 0 | 0 | 0 | 0 | 0 | 0 | 0 | 0 | 5 | 3 | 0 | 8 | 4 | 9 | 9 | 9 | 7 | 0 | 0 | 7 | 2 | 2 | 8 | 9 | 0 |
| | | | | | | | | | 1 | 2 | 0 | 2 | 2 | 6 | 8 | 8 | 7 | 0 | 0 | 5 | 0 | 0 | 7 | 2 | 0 |
| 12 | 0 | 0 | 0 | 0 | 0 | 0 | 0 | 0 | 5 | 7 | 6 | 8 | 4 | 7 | 9 | 9 | 6 | 2 | 0 | 8 | 4 | 2 | 7 | 9 | 2 |
| | | | | | | | | | 1 | 5 | 4 | 8 | 2 | 7 | 8 | 9 | 6 | 0 | 0 | 8 | 2 | 0 | 7 | 8 | 0 |
| 13 | 0 | 0 | 0 | 0 | 0 | 0 | 0 | 0 | 5 | 7 | 7 | 8 | 7 | 8 | 9 | 9 | 7 | 0 | 0 | 8 | 5 | 2 | 8 | 8 | 0 |
| | | | | | | | | | 1 | 6 | 5 | 8 | 7 | 7 | 8 | 9 | 7 | 0 | 0 | 8 | 4 | 1 | 7 | 8 | 0 |
| 14 | 0 | 0 | 0 | 0 | 0 | 0 | 0 | 0 | 5 | 6 | 0 | 8 | 7 | 4 | 9 | 9 | 6 | 0 | 0 | 7 | 4 | 0 | 8 | 8 | 0 |
| | | | | | | | | | 1 | 5 | 0 | 8 | 6 | 3 | 9 | 9 | 6 | 0 | 0 | 7 | 2 | 0 | 8 | 7 | 0 |
| 15 | 0 | 0 | 6 | 0 | 0 | 7 | 1 | 0 | 5 | 6 | 2 | 8 | 7 | 6 | 8 | 8 | 7 | 0 | 0 | 8 | 5 | 4 | 9 | 9 | 2 |
| | | | | | | | | | 1 | 2 | 0 | 8 | 6 | 5 | 7 | 8 | 5 | 0 | 0 | 7 | 4 | 0 | 8 | 8 | 0 |
| 16 | 0 | 0 | 7 | 0 | 0 | 7 | 0 | 0 | 5 | 2 | 0 | 7 | 4 | 6 | 7 | 8 | 6 | 4 | 0 | 8 | 2 | 4 | 9 | 8 | 2 |
| | | | | | | | | | 1 | 0 | 0 | 5 | 2 | 4 | 7 | 8 | 5 | 3 | 0 | 7 | 0 | 0 | 8 | 7 | 0 |
| 17 | 0 | 0 | 0 | 0 | 1 | 4 | 0 | 0 | 5 | 2 | 0 | 7 | 2 | 6 | 7 | 8 | 5 | 2 | 0 | 6 | 2 | 1 | 7 | 2 | 0 |
| | | | | | | | | | 1 | 0 | 0 | 5 | 0 | 2 | 7 | 8 | 2 | 0 | 0 | 2 | 0 | 0 | 4 | 0 | 0 |
| 18 | 0 | 0 | 5 | 2 | 0 | 7 | 0 | 0 | 5 | 0 | 0 | 2 | 0 | 4 | 7 | 6 | 5 | 0 | 0 | 2 | 0 | 1 | 4 | 5 | 2 |
| | | | | | | | | | 1 | 0 | 0 | 0 | 0 | 0 | 6 | 6 | 2 | 0 | 0 | 2 | 0 | 0 | 2 | 4 | 0 |
| 25 | 5 | 4 | 7 | 5 | 3 | 6 | 6 | 0 | 5 | 6 | 7 | 7 | 5 | 4 | 8 | 8 | 6 | 0 | 0 | 4 | 2 | 0 | 6 | 4 | 2 |
| | | | | | | | | | 1 | 5 | 5 | 6 | 2 | 4 | 8 | 8 | 6 | 0 | 0 | 2 | 0 | 0 | 5 | 2 | 0 |
| 26 | 0 | 0 | 6 | 5 | 1 | 4 | 4 | 0 | 5 | 6 | 2 | 8 | 7 | 7 | 8 | 9 | 7 | 0 | 0 | 7 | 0 | 0 | 7 | 7 | 0 |
| | | | | | | | | | 1 | 5 | 1 | 7 | 6 | 6 | 8 | 9 | 6 | 0 | 0 | 6 | 0 | 0 | 6 | 6 | 0 |
| 27 | 0 | 0 | 0 | 0 | 0 | 0 | 0 | 0 | 5 | 7 | 0 | 7 | 4 | 6 | 7 | 9 | 6 | 0 | 0 | 4 | 0 | 0 | 8 | 6 | 0 |
| | | | | | | | | | 1 | 2 | 0 | 5 | 2 | 5 | 7 | 8 | 5 | 0 | 0 | 2 | 0 | 0 | 7 | 5 | 0 |
| 28 | 0 | 0 | 0 | 0 | 0 | 0 | 0 | 0 | 5 | 4 | 2 | 9 | 7 | 6 | 7 | 7 | 5 | 2 | 0 | 7 | 0 | 0 | 5 | 2 | 2 |
| | | | | | | | | | 1 | 2 | 0 | 5 | 5 | 2 | 7 | 7 | 4 | 0 | 0 | 5 | 0 | 0 | 4 | 0 | 0 |
| 29 | 2 | 0 | 5 | 0 | 4 | 2 | 3 | 0 | 5 | 7 | 0 | 8 | 7 | 5 | 8 | 8 | 5 | 2 | 0 | 6 | 0 | 0 | 7 | 5 | 2 |
| | | | | | | | | | 1 | 5 | 0 | 7 | 6 | 4 | 8 | 7 | 2 | 0 | 0 | 4 | 0 | 0 | 5 | 4 | 0 |
| 30 | 5 | 6 | 7 | 4 | 3 | 8 | 8 | 2 | 5 | 0 | 0 | 0 | 6 | 8 | 5 | 6 | 5 | 0 | 4 | 3 | 2 | 6 | 9 | 0 |
| | | | | | | | | | 1 | 0 | 0 | 0 | 5 | 7 | 4 | 5 | 0 | 0 | 0 | 0 | 0 | 5 | 2 | 0 |
| 31 | 7 | 5 | 7 | 5 | 7 | 6 | 7 | 5 | 5 | 0 | 0 | 0 | 0 | 5 | 9 | 6 | 8 | 6 | 0 | 8 | 2 | 2 | 7 | 8 | 5 |
| | | | | | | | | | 1 | 0 | 0 | 0 | 0 | 4 | 7 | 5 | 7 | 2 | 0 | 4 | 0 | 0 | 2 | 7 | 2 |
| 32 | 5 | 6 | 8 | 7 | 4 | 7 | 8 | 0 | 5 | 5 | 0 | 7 | 5 | 6 | 9 | 9 | 5 | 0 | 0 | 8 | 2 | 1 | 8 | 8 | 0 |
| | | | | | | | | | 1 | 5 | 0 | 6 | 4 | 5 | 8 | 9 | 4 | 0 | 0 | 7 | 0 | 0 | 7 | 8 | 0 |
| 33 | 3 | 5 | 7 | 4 | 5 | 8 | 7 | 0 | 5 | 4 | 0 | 5 | 3 | 4 | 9 | 9 | 5 | 0 | 0 | 6 | 2 | 2 | 8 | 9 | 0 |
| | | | | | | | | | 1 | 3 | 0 | 4 | 2 | 3 | 8 | 9 | 4 | 0 | 0 | 6 | 0 | 1 | 7 | 8 | 0 |
| 34 | 4 | 3 | 5 | 4 | 3 | 9 | 9 | 5 | 5 | 4 | 0 | 6 | 4 | 7 | 9 | 9 | 7 | 0 | 0 | 6 | 2 | 1 | 9 | 9 | 5 |
| | | | | | | | | | 1 | 2 | 0 | 2 | 3 | 5 | 8 | 9 | 6 | 0 | 0 | 5 | 0 | 0 | 8 | 8 | 4 |
| 35 | 6 | 5 | 6 | 6 | 1 | 5 | 4 | 0 | 5 | 6 | 7 | 8 | 6 | 8 | 8 | 9 | 6 | 4 | 2 | 8 | 5 | 6 | 8 | 9 | 2 |
| | | | | | | | | | 1 | 5 | 2 | 8 | 6 | 7 | 8 | 8 | 5 | 2 | 0 | 8 | 4 | 5 | 8 | 9 | 0 |
| 36 | 3 | 0 | 2 | 5 | 0 | 3 | 0 | 0 | 5 | 4 | 0 | 7 | 5 | 6 | 8 | 8 | 5 | 1 | 0 | 5 | 0 | 2 | 7 | 7 | 0 |
| | | | | | | | | | 1 | 3 | 0 | 6 | 4 | 6 | 7 | 8 | 4 | 0 | 0 | 4 | 0 | 1 | 6 | 7 | 0 |
| 37 | 6 | 5 | 7 | 6 | 1 | 7 | 8 | 0 | 5 | 6 | 7 | 8 | 7 | 6 | 8 | 9 | 6 | 4 | 5 | 8 | 6 | 4 | 8 | 9 | 4 |
| | | | | | | | | | 1 | 5 | 4 | 7 | 6 | 5 | 8 | 8 | 5 | 2 | 2 | 7 | 5 | 2 | 6 | 9 | 2 |
| 38 | 6 | 4 | 7 | 3 | 5 | 5 | 6 | 2 | 5 | 2 | 0 | 7 | 4 | 3 | 8 | 8 | 6 | 2 | 0 | 6 | 4 | 1 | 5 | 6 | 0 |
| | | | | | | | | | 1 | 0 | 0 | 4 | 0 | 3 | 7 | 8 | 5 | 0 | 0 | 5 | 0 | 0 | 4 | 5 | 0 |
| 39 | 7 | 4 | 7 | 6 | 6 | 7 | 7 | 6 | 5 | 4 | 0 | 8 | 4 | 4 | 8 | 8 | 7 | 6 | 4 | 6 | 4 | 2 | 7 | 6 | 4 |

TABLE 9-continued

| Compound of Ex. No. | Soil drench 10 kg/ha Mz | R | BG | O | L | M | SB | S | Dosage kg/ha | Foliar spray Mz | R | BG | O | L | M | SB | S | Pre-emergence Mz | R | BG | O | L | M | SB | S |
|---|---|---|---|---|---|---|---|---|---|---|---|---|---|---|---|---|---|---|---|---|---|---|---|---|---|
| | | | | | | | | | 1 | 2 | 0 | 6 | 2 | 4 | 8 | 8 | 6 | 2 | 0 | 5 | 2 | 0 | 5 | 6 | 0 |
| 40 | 0 | 0 | 0 | 0 | 0 | 0 | 0 | 0 | 5 | 0 | 0 | 0 | 0 | 0 | 4 | 5 | 0 | 0 | 0 | 0 | 0 | 0 | 0 | 0 | 0 |
| | | | | | | | | | 1 | 0 | 0 | 0 | 0 | 0 | 2 | 5 | 0 | 0 | 0 | 0 | 0 | 0 | 0 | 0 | 0 |
| 41 | 0 | 0 | 7 | 2 | 0 | 0 | 0 | 0 | 5 | 5 | 0 | 8 | 6 | 0 | 7 | 8 | 4 | 0 | 0 | 0 | 0 | 0 | 0 | 0 | 0 |
| | | | | | | | | | 1 | 2 | 0 | 8 | 5 | 0 | 4 | 5 | 4 | 0 | 0 | 0 | 0 | 0 | 0 | 0 | 0 |
| 42 | 0 | 0 | 6 | 2 | 0 | 0 | 0 | 0 | 5 | 4 | 0 | 3 | 4 | 0 | 0 | 0 | 0 | 0 | 0 | 0 | 0 | 0 | 0 | 0 | 0 |
| | | | | | | | | | 1 | 0 | 0 | 3 | 4 | 0 | 0 | 0 | 0 | 0 | 0 | 0 | 0 | 0 | 0 | 0 | 0 |
| 43 | 0 | 0 | 0 | 0 | 0 | 0 | 0 | 0 | 5 | 2 | 0 | 5 | 1 | 0 | 0 | 0 | 0 | 0 | 0 | 0 | 0 | 0 | 0 | 0 | 0 |
| | | | | | | | | | 1 | 0 | 0 | 4 | 0 | 0 | 0 | 0 | 0 | 0 | 0 | 0 | 0 | 0 | 0 | 0 | 0 |
| 44 | 0 | 0 | 0 | 0 | 0 | 0 | 0 | 0 | 5 | 0 | 0 | 2 | 1 | 0 | 0 | 2 | 0 | 0 | 0 | 0 | 0 | 0 | 0 | 0 | 0 |
| | | | | | | | | | 1 | 0 | 0 | 0 | 0 | 0 | 0 | 0 | 0 | 0 | 0 | 0 | 0 | 0 | 0 | 0 | 0 |
| 45 | 0 | 0 | 0 | 0 | 0 | 0 | 0 | 0 | 5 | 4 | 0 | 6 | 4 | 3 | 5 | 6 | 2 | 0 | 0 | 0 | 0 | 0 | 0 | 0 | 0 |
| | | | | | | | | | 1 | 2 | 0 | 5 | 0 | 0 | 2 | 5 | 0 | 0 | 0 | 0 | 0 | 0 | 0 | 0 | 0 |
| 46 | 0 | 0 | 0 | 0 | 0 | 0 | 0 | 0 | 5 | 4 | 6 | 4 | 0 | 0 | 5 | 6 | 2 | 0 | 0 | 0 | 0 | 0 | 0 | 0 | 0 |
| | | | | | | | | | 1 | 0 | 2 | 0 | 0 | 0 | 2 | 2 | 0 | 0 | 0 | 0 | 0 | 0 | 0 | 0 | 0 |
| 47 | 0 | 0 | 5 | 4 | 0 | 0 | 0 | 0 | 5 | 4 | 0 | 7 | 4 | 2 | 5 | 6 | 5 | 0 | 0 | 0 | 0 | 0 | 0 | 0 | 0 |
| | | | | | | | | | 1 | 3 | 0 | 5 | 4 | 0 | 2 | 5 | 2 | 0 | 0 | 0 | 0 | 0 | 0 | 0 | 0 |
| 48 | 0 | 0 | 3 | 0 | 0 | 0 | 0 | 0 | 5 | 2 | 0 | 6 | 2 | 0 | 0 | 6 | 0 | 0 | 0 | 0 | 0 | 0 | 0 | 0 | 0 |
| | | | | | | | | | 1 | 0 | 0 | 2 | 0 | 0 | 0 | 2 | 0 | 0 | 0 | 0 | 0 | 0 | 0 | 0 | 0 |
| 49 | 0 | 0 | 5 | 4 | 0 | 0 | 0 | 0 | 5 | 3 | 0 | 7 | 5 | 0 | 4 | 6 | 7 | 0 | 0 | 0 | 0 | 0 | 0 | 0 | 0 |
| | | | | | | | | | 1 | 2 | 0 | 6 | 4 | 0 | 2 | 5 | 4 | 0 | 0 | 0 | 0 | 0 | 0 | 0 | 0 |

We claim:

1. A compound of the formula

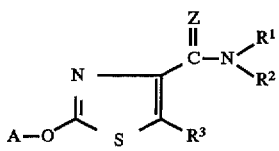

in which A represents a trifluoromethylphenyl group, a chloropyridyl group or a pyrazolyl group of the formula

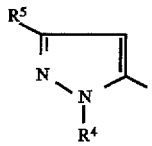

in which $R^4$ represents a methyl group and $R^5$ represents trifluoromethyl group;

Z represents an oxygen or sulphur atom; $R^1$ and $R^2$ each independently represents a hydrogen atom or an optionally substituted alkyl, alkenyl, alkynyl, cycloalkyl, cycloalkylalkyl, heterocyclyl, aryl, aralkyl, alkaryl, hydroxy, alkoxy, alkenyloxy, alkynyloxy, alkylcarbonyl, alkoxycarbonyl, animo, mono-or di-alkylamino, alkoxycarbonylamino, arylamino, arylalkylamino or dialkylcarbamoyl group, or together represent an alkylene chain which is optionally interrupted by an oxygen or sulphur atom or by a group —NR— in which R represents a hydrogen atom or an alkyl group; and $R^3$ represents a hydrogen or halogen atom or an alkyl group.

2. The compound of claim 1 wherein Z is an oxygen atom.

3. A compound of the formula

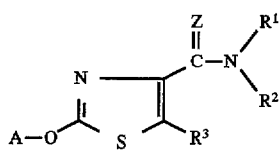

wherein A represents a group of the formula

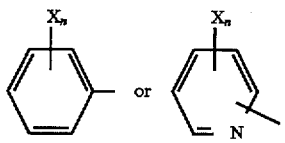

in which each X independently represents a halogen atom or an optionally substituted alkyl, cycloalkyl, alkoxy, aryl or aryloxy group, or an alkenyloxy, alkynyloxy, alkylthio, haloalkylthio, alkenylthio, alkynylthio, alkylsulphinyl, alkylsulphonyl or cyano group; and n is 0, an integer from 1 to 4, or, for the phenyl group, 5; or A represents a group of the formula

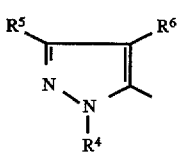

in which each of $R^4$, $R^5$ and $R^6$ independently represents a hydrogen or halogen atom, an optionally substituted alkyl, alkenyl, alkynyl, cycloalkyl, cycloalkylalkyl, aryl, aralkyl, alkaryl, alkoxy; amino, mono- or di-alkylamino, alkoxycarbonylamino, arylamino, dialkylcarbamoyl, acyl or acylamido group or a cyano group, with the proviso that $R^5$ and $R^6$ do not represent an acyl, acylamido or cyano group;

Z represents an oxygen or sulphur atom; one of $R^1$ and $R^2$ represents a hydrogen atom or a $C_{1-4}$ alkyl group and the other represents a $C_{1-6}$ alkyl, $C_{1-4}$ fluoroalkyl, phen-$(C_{1-2})$ alkyl, thienyl $(C_{1-2})$alkyl, cyclopropyl $(C_{1-2})$alkyl, $C_{1-4}$ alkoxy; cyclopropyl, cyclobutyl, morpholino, phenyl or mono- or di-fluorophenyl group; and $R^3$ represents a hydrogen or halogen atom or an alkyl group.

4. The compound of claim 3 wherein Z is an oxygen atom.

5. A method of combating undesired plant growth at a locus, which comprises treating the locus with a herbicidal composition comprising a compound of the formula

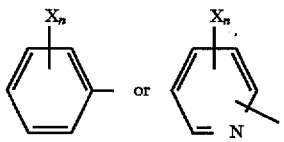

wherein A represents a group of the formula

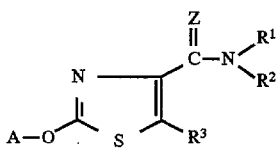

in which each X independently represents a halogen atom or an optionally substituted alkyl, cycloalkyl, alkoxy, aryl or aryloxy group, or an alkenyloxy, alkynyloxy, alkylthio, haloalkylthio, alkenylthio, alkynylthio, alkylsulphinyl, alkylsulphonyl or cyano group; and n is 0, an integer from 1 to 4, or, for the phenyl group, 5; or A represents a group of the formula

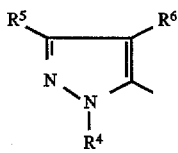

in which each of $R^4$, $R^5$ and $R^6$ independently represents a hydrogen or halogen atom, an optionally substituted alkyl, alkenyl, alkynyl, cycloalkyl, cycloalkylalkyl, aryl, aralkyl, alkaryl, alkoxy, amino, mono- or di-alkylamino, alkoxycarbonylamino, arylamino, dialkylcarbamoyl, acyl or acylamido group or a cyano group, with the proviso that $R^5$ and $R^6$ do not represent an acyl, acylamido or cyano group;

Z represents an oxygen or sulphur atom; $R^1$ and $R^2$ each independently represents a hydrogen atom or an optionally substituted alkyl, alkenyl, alkynyl, cycloalkyl, cycloalkylalkyl, heterocyclyl, aryl, aralkyl, alkaryl, hydroxy, alkoxy, alkenyloxy, alkynyloxy, alkylcarbonyl, alkoxycarbonyl, animo, mono- or di-alkylamino, alkoxycarbonylamino, arylamino, arylalkylamino or dialkylcarbamoyl group, or together represent an alkylene chain which is optionally interrupted by an oxygen or sulphur atom or by a group —NR— in which R represents a hydrogen atom or an alkyl group; and $R^3$ represents a hydrogen or halogen atom or an alkyl group; and a carrier.

6. The method of claim 5 wherein Z in the compound is an oxygen atom.

* * * * *